(12) United States Patent
Rashid et al.

(10) Patent No.: US 10,556,847 B2
(45) Date of Patent: Feb. 11, 2020

(54) PROCESSES AND APPARATUSES FOR METHYLATION OF AROMATICS IN AN AROMATICS COMPLEX

(71) Applicant: UOP LLC, Des Plaines, IL (US)

(72) Inventors: Naiyl A. Rashid, Carpentersville, IL (US); Gregory B. Kuzmanich, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/100,010

(22) Filed: Aug. 9, 2018

(65) Prior Publication Data

US 2019/0169096 A1   Jun. 6, 2019

Related U.S. Application Data

(60) Provisional application No. 62/595,381, filed on Dec. 6, 2017.

(51) Int. Cl.
| | | |
|---|---|---|
| C07C 15/08 | (2006.01) | |
| C07C 2/64 | (2006.01) | |
| C07C 2/86 | (2006.01) | |
| C07C 6/12 | (2006.01) | |
| C07C 15/04 | (2006.01) | |
| C07C 15/06 | (2006.01) | |

(52) U.S. Cl.
CPC ............. *C07C 15/08* (2013.01); *C07C 2/64* (2013.01); *C07C 2/864* (2013.01); *C07C 6/126* (2013.01); *C07C 15/04* (2013.01); *C07C 15/06* (2013.01); *C07C 2529/40* (2013.01)

(58) Field of Classification Search
CPC ......... C07C 15/04; C07C 15/06; C07C 15/08; C07C 2/64
See application file for complete search history.

(56) References Cited

U.S. PATENT DOCUMENTS

2015/0073187 A1   3/2015   Ghosh et al.

FOREIGN PATENT DOCUMENTS

| CN | 104557428 A | 4/2015 |
| WO | 2017105848 A1 | 6/2017 |

OTHER PUBLICATIONS

International Search Report and Written Opinion from corresponding PCT Application No. PCT/US2018/064031, dated Mar. 21, 2019.

*Primary Examiner* — In Suk C Bullock
*Assistant Examiner* — Jason Y Chong

(57) ABSTRACT

This present disclosure relates to processes and apparatuses for methylation of aromatics in an aromatics complex for producing a xylene isomer product. More specifically, the present disclosure relates to processes and apparatuses for producing para-xylene by the selective methylation of toluene and/or benzene in an aromatics complex using processed toluene instead of crude toluene.

8 Claims, 2 Drawing Sheets

US 10,556,847 B2

PROCESSES AND APPARATUSES FOR METHYLATION OF AROMATICS IN AN AROMATICS COMPLEX

CROSS-REFERENCE TO RELATED APPLICATION

This application claims priority from U.S. Provisional Application No. 62/595,381 filed Dec. 6, 2017, the contents of which cited application are hereby incorporated by reference in its entirety.

FIELD

This present disclosure relates to processes and apparatuses for methylation of aromatics in an aromatics complex for producing a xylene isomer product. More specifically, the present disclosure relates to a process for producing para-xylene by the selective methylation of toluene and/or benzene in an aromatics complex.

BACKGROUND

Xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. Ethylbenzene generally is present in xylene mixtures and is occasionally recovered for styrene production, but is usually considered a less-desirable component of C8 aromatics.

Among the aromatic hydrocarbons, the overall importance of xylenes rivals that of benzene as a feedstock for industrial chemicals. Xylenes and benzene are produced from petroleum by reforming naphtha but not in sufficient volume to meet demand, thus conversion of other hydrocarbons is necessary to increase the yield of xylenes and benzene. Often toluene is de-alkylated to produce benzene or selectively disproportionated to yield benzene and C8 aromatics from which the individual xylene isomers are recovered.

An aromatics complex flow scheme has been disclosed by Meyers in the HANDBOOK OF PETROLEUM REFINING PROCESSES, 2d. Edition in 1997 by McGraw-Hill, and is incorporated herein by reference.

Traditional aromatics complexes send toluene to a transalkylation zone to generate desirable xylene isomers via transalkylation of the toluene with A9+ components. A9+ components are present in both the reformate bottoms and the transalkylation effluent.

Methylation of toluene or benzene with oxygenates such as methanol has been proposed as a pathway to make xylene and to increase methyl to phenyl ratio in the aromatic complex to maximize xylene production. Toluene methylation operating in vapor phase has a poor feed, especially oxygenate, utilization, low aromatics conversion per pass and poor catalyst stability in a time span of hours, days and weeks, thus requiring frequent regeneration. Typically, toluene methylation is operating with selective para-xylene production objective, which requires operating under severe process conditions, namely high temperature where methanol decomposition to COx and H2 is significant, with a significant amount of diluents such as $H_2O$ and $H_2$ and thus requires recycling a catalyst which is relatively difficult to prepare reproducibly. MFI zeolite has been the catalyst being used predominantly in this process.

Toluene methylation can greatly increase the para-xylene production of an aromatic complex. However, the toluene methylation catalyst cannot effectively process un-extracted toluene. If toluene methylation uses unextracted toluene, non-aromatics can build up in the toluene methylation loop to nearly 25% of the feed. This represents a loss of capacity from a state of the art toluene methylation unit. To avoid this, toluene is traditionally extracted using an aromatics extraction unit, but an aromatics extraction unit is an expensive unit to run.

Accordingly, it is desirable to provide improved methods and apparatuses for methylation of aromatic compounds such as toluene and benzene in an aromatics complex. Further, it is desirable to provide a cost-effective method and apparatus for toluene and/or benzene methylation which operates under mild condition, promotes high utilization of the feedstock and where higher than equilibrium para-xylene to xylene can be achieved without using dilution. Also, it is desirable to reduce the overall costs of operating and/or incorporating such a methylation unit in an aromatics complex. Furthermore, other desirable features and characteristics of the present subject matter will become apparent from the subsequent detailed description of the subject matter and the appended claims, taken in conjunction with the accompanying drawings and this background of the subject matter.

SUMMARY

The present subject matter relates to processes and apparatuses for toluene and/or benzene methylation in an aromatics complex for producing xylene isomer. More specifically, the present disclosure relates to processes and apparatuses for toluene methylation wherein instead of using an aromatics extraction unit to extract toluene, toluene methylation can effectively use toluene that has been passed over a transalkylation catalyst once. This processed toluene can then to fed to the toluene methylation unit without building up non-aromatics over time. If unextracted toluene is used, a build-up of non-aromatics occurs resulting in about a 25% decrease in toluene methylation throughput.

In the foregoing, all temperatures are set forth in degrees Celsius and all parts and percentages are by weight, unless otherwise indicated. Other objects, advantages and applications of the present invention will become apparent to those skilled in the art from the following detailed description and drawing. Additional objects, advantages and novel features of the examples will be set forth in part in the description which follows, and in part will become apparent to those skilled in the art upon examination of the following description and the accompanying drawing or may be learned by production or operation of the examples. The objects and advantages of the concepts may be realized and attained by means of the methodologies, instrumentalities and combinations particularly pointed out in the appended claims.

DEFINITIONS

Figure 1:
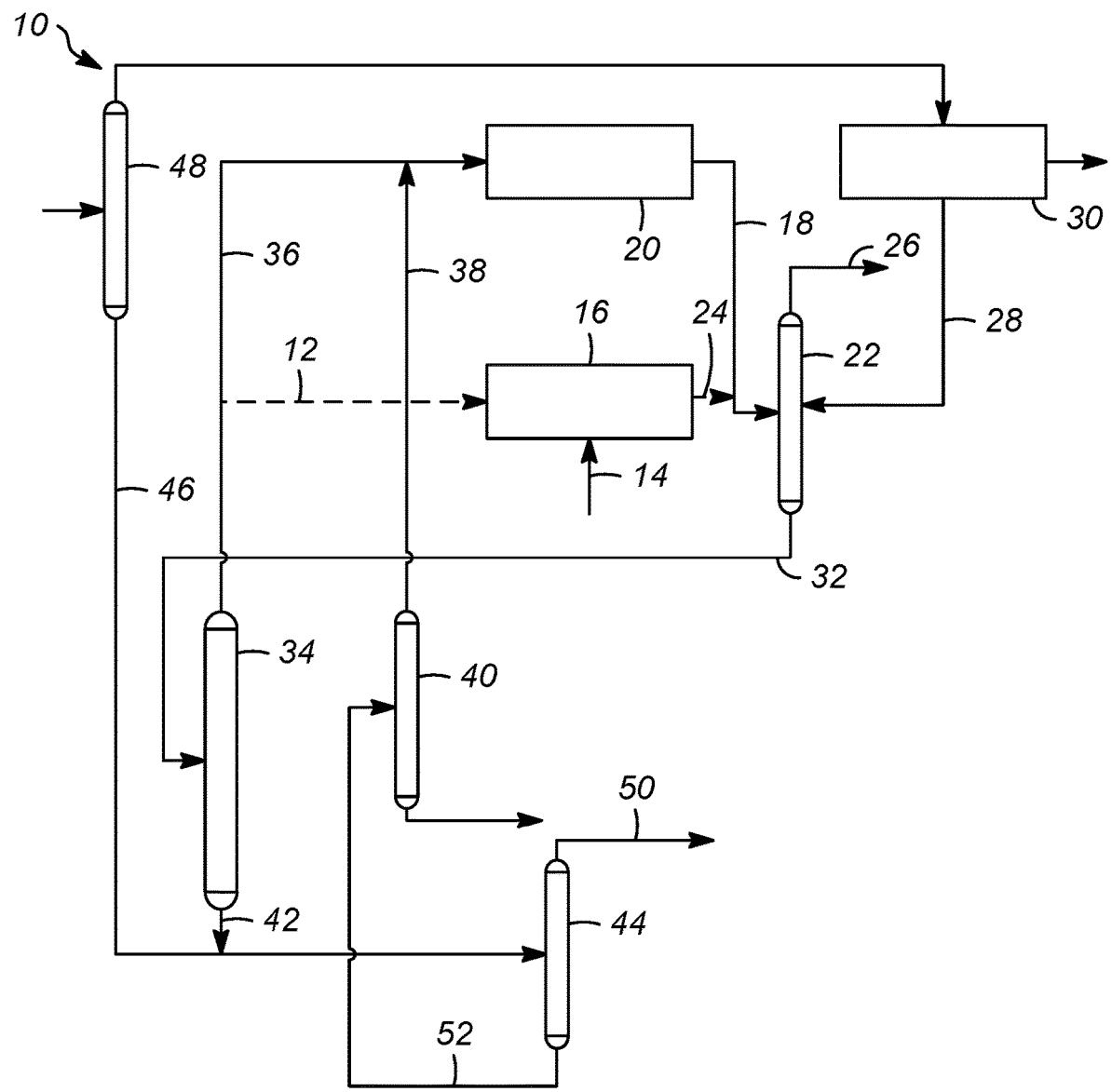
FIG. 1 illustrates a process and apparatus for toluene methylation demonstrated in the prior art.

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

As used herein, the term "overhead stream" can mean a stream withdrawn at or near a top of a vessel, such as a column.

As used herein, the term "bottoms stream" can mean a stream withdrawn at or near a bottom of a vessel, such as a column.

Hydrocarbon molecules may be abbreviated C1, C2, C3, Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8, An where "n" represents the number of carbon atoms in the one or more aromatic molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three or more carbon atoms.

As used herein, the term "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top or overhead pressure is the pressure of the overhead vapor at the vapor outlet of the column. The bottom temperature is the liquid bottom outlet temperature. Net overhead lines and net bottoms lines refer to the net lines from the column downstream of any reflux or reboil to the column unless otherwise shown. Stripping columns may omit a reboiler at a bottom of the column and instead provide heating requirements and separation impetus from a fluidized inert media such as steam.

As depicted, process flow lines in the drawings can be referred to interchangeably as, e.g., lines, pipes, feeds, gases, products, discharges, parts, portions, or streams.

The term "passing" means that the material passes from a conduit or vessel to an object.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The description of the apparatus of this invention is presented with reference to the attached Figures. The Figures are simplified diagrams of the preferred embodiment of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

The various embodiments described herein relate to processes and apparatuses for toluene and/or benzene methylation in an aromatics complex for producing xylene isomer. FIG. 1 illustrates the current state of the art. As shown in FIG. 1, a process and apparatus 10 comprises of a first feed stream 12 comprising unextracted toluene and a second feed stream 14 comprising methanol. Unextracted toluene may contain up to 40% by weight non-aromatics that co-boil with the toluene. The first feed stream 12 and the second feed stream 14 are combined and pass to a toluene methylation reaction zone 16. Additional methanol streams may be fed to the toluene methylation reaction zone 16. It is also contemplated that additional methanol streams may also be added to the toluene methylation reaction zone 16. The toluene methylation reaction zone 16 may comprise multiple reactors. The toluene methylation reaction zone 16 may comprise only one reactor or one reactor with interstage injection points to control the reactor exotherm, or the toluene methylation reaction zone 16 may comprise up to four reactors. The toluene methylation reaction zone 16 operates at under standard toluene methylation operating conditions.

The toluene methylation reaction zone product stream 24 exits the toluene methylation reaction zone 16 and contacts a stream 18 originating from a transalkylation zone 20 and passes to a benzene column 22. A stream 28 that originates from the aromatics extraction unit is also sent to the benzene column 22. A benzene stream 26 exits the top of the benzene column 22. The benzene column bottoms stream 32 exits the benzene column 22 and enters the toluene column 34. The overhead stream 36 from the toluene column enters the transalkylation zone 20 along with stream 38 which is the overhead stream from the heavy aromatics column 40. The bottoms stream 42 from the toluene column 34 is sent to a xylene column along with stream 46 which is the bottoms stream from the reformate stripper 48. The overhead stream 50 is sent to para-xylene purification and the bottoms stream 52 is sent to the heavy aromatics column 40.

Figure 2:
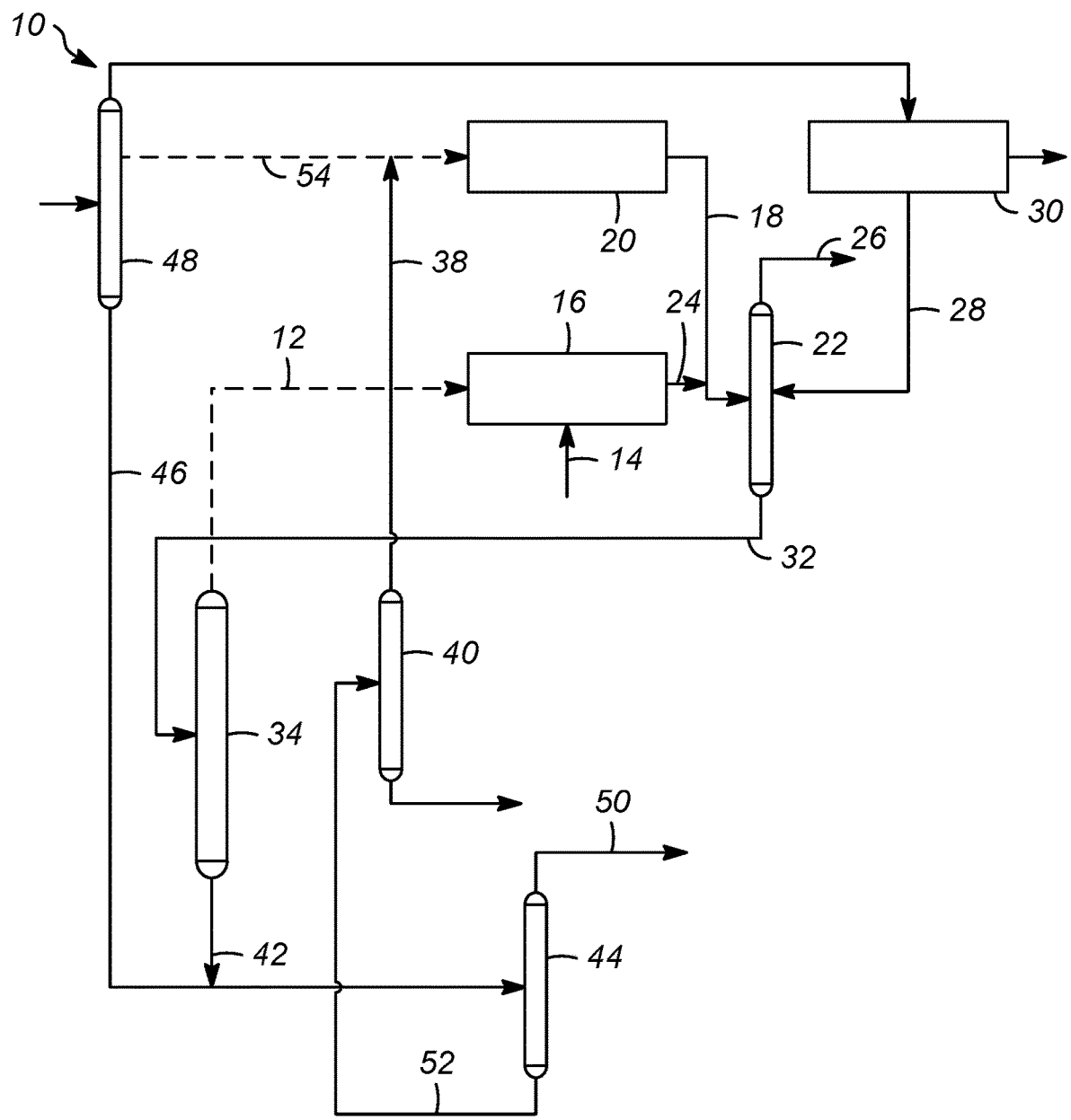
FIG. 2 illustrates a process and apparatus for toluene methylation according the claimed invention.

Now turning to FIG. 2, a lot of the units are the same, but here instead of sending the overhead stream from the toluene column 34 to the transalkylation unit 20, the overhead from the toluene column is sent to the toluene methylation unit 16 as illustrated in line 12 and a stream 54 form the reformate splitter 48 is sent to the transalkylation catalyst once. This processed toluene can then to fed to the toluene methylation unit 16 without building up non-aromatics occurs over time. If unextracted toluene is used, a build-up of non-aromatic occurs resulting in about a 25% decrease in toluene methylation throughput. Processed toluene may contain 10% or less non-aromatics.

While the invention has been described with what are presently considered the preferred embodiments, it is to be understood that the invention is not limited to the disclosed embodiments, but it is intended to cover various modifications and equivalent arrangements included within the scope of the appended claims.

Specific Embodiments

While the following is described in conjunction with specific embodiments, it will be understood that this description is intended to illustrate and not limit the scope of the preceding description and the appended claims.

A first embodiment of the invention is a process for the methylation of toluene, comprising passing a processed toluene stream and a methanol feed stream to a toluene methylation reaction zone to produce a toluene methylation reaction zone product stream; passing a stream comprising crude A7 and unextracted toluene and an overhead stream from a heavy aromatics column to a transalkylation reaction zone to produce a transalkyation product stream; and passing the toluene methylation reaction zone product stream and the transalkyation product stream to a benzene column. An embodiment of the invention is one, any or all of prior embodiments in this paragraph up through the first embodiment in this paragraph, wherein the processed toluene stream and at least one methanol stream are admixed before entering the reaction zone. An embodiment of the invention is one, any or all of prior embodiments in this paragraph up through the first embodiment in this paragraph, wherein additional methanol streams are passed to the toluene methylation reaction zone. An embodiment of the invention is one, any or all of prior embodiments in this paragraph up through the first embodiment in this paragraph, wherein the reaction zone comprises at least one reactor. An embodiment of the invention is one, any or all of prior embodiments in this paragraph up through the first embodiment in this paragraph, wherein the reaction zone comprises no more than four reactors. An embodiment of the invention is one, any or all of prior embodiments in this paragraph up through the first embodiment in this paragraph, wherein the processed toluene may comprise less than about 5% non-aromatics. An embodiment of the invention is one, any or all of prior embodiments in this paragraph up through the first embodiment in this paragraph, wherein the processed toluene may comprise less than about 1% non-aromatics. An embodiment of the invention is one, any or all of prior embodiments in this paragraph up through the first embodiment in this paragraph, wherein the processed toluene may comprise less than about 0.25% non-aromatics.

A second embodiment of the invention is an apparatus for the methylation of toluene, comprising a line comprising processed toluene from the toluene column in direct communication with a toluene methylation reaction zone, a line comprising methanol in direct communication with the toluene methylation zone, wherein the reaction zone is also coupled to a line comprising the reaction zone product stream; An embodiment of the invention is one, any or all of prior embodiments in this paragraph up through the second embodiment in this paragraph, wherein the processed toluene stream and at least one methanol stream are admixed before entering the reaction zone. An embodiment of the invention is one, any or all of prior embodiments in this paragraph up through the second embodiment in this paragraph, wherein additional methanol streams are passed to the toluene methylation reaction zone. An embodiment of the invention is one, any or all of prior embodiments in this paragraph up through the second embodiment in this paragraph, wherein the reaction zone comprises at least one reactor. An embodiment of the invention is one, any or all of prior embodiments in this paragraph up through the second embodiment in this paragraph, wherein the reaction zone comprises no more than four reactors. An embodiment of the invention is one, any or all of prior embodiments in this paragraph up through the second embodiment in this paragraph, wherein the processed toluene may comprise less than about 5% non-aromatics. An embodiment of the invention is one, any or all of prior embodiments in this paragraph up through the second embodiment in this paragraph, wherein the processed toluene may comprise less than about 1% non-aromatics. An embodiment of the invention is one, any or all of prior embodiments in this paragraph up through the second embodiment in this paragraph, wherein the processed toluene may comprise less than about 0.25% non-aromatics.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for the methylation of toluene in an aromatics complex, comprising:
   passing a stream comprising crude A7 and an overhead stream comprising A9+ from a heavy aromatics column to a transalkylation reaction zone to produce a transalkylation product stream comprising xylene isomers, wherein the stream comprising crude A7 further includes up to 40% by weight non-aromatic toluene co-boilers;
   passing a processed toluene stream and a methanol feed stream to a toluene methylation reaction zone to produce a toluene methylation reaction zone product stream comprising xylene isomers;
   passing the toluene methylation reaction zone product stream and the transalkylation product stream to a benzene column to obtain a benzene column overhead stream comprising benzene and a benzene column bottoms stream comprising A7+;
   passing the benzene column bottoms stream comprising A7+ to a toluene column to obtain a toluene column overhead stream comprising toluene and a toluene column bottoms stream comprising A8+, wherein the processed toluene stream is the toluene column overhead stream;
   passing the toluene column bottoms to a xylene column to obtain a xylene column overhead stream comprising A8 and a xylene column bottoms stream comprising A9+; and
   passing the xylene column bottoms stream to the heavy aromatics column.

2. The process of claim 1, wherein the processed toluene stream and at least one methanol stream are admixed before entering the reaction zone.

3. The process of claim 1, wherein additional methanol streams are passed to the toluene methylation reaction zone.

4. The process of claim 1, wherein the reaction zone comprises at least one reactor.

5. The process of claim 1, wherein the reaction zone comprises no more than four reactors.

6. The process of claim 1, wherein the processed toluene may comprise less than about 5% non-aromatics.

7. The process of claim 1, wherein the processed toluene may comprise less than about 1% non-aromatics.

8. The process of claim 1, wherein the processed toluene may comprise less than about 0.25% non-aromatics.

\* \* \* \* \*